United States Patent [19]
Alpern et al.

[11] Patent Number: 5,284,240
[45] Date of Patent: Feb. 8, 1994

[54] NO TOUCH SUTURE PACKAGE

[75] Inventors: Marvin Alpern, Glen Ridge, N.J.; Robert Cerwin, Pipersville; Joseph Pergine, Chalfont, both of Pa.

[73] Assignee: Ethicon, Inc., Somerville, N.J.

[21] Appl. No.: 8,444

[22] Filed: Jan. 22, 1993

[51] Int. Cl.⁵ ............................................. A61B 17/06
[52] U.S. Cl. ........................................ 206/63.3; 206/380
[58] Field of Search .................... 206/63.3, 63.5, 227, 206/380, 383, 388, 389, 408, 409, 495

[56] References Cited

U.S. PATENT DOCUMENTS

| 4,412,613 | 11/1983 | Kubas | 206/63.3 |
| 4,519,501 | 5/1985 | Cerwin | 206/63.3 |
| 4,549,649 | 10/1985 | Roshdy | 206/63.3 |
| 4,967,902 | 11/1990 | Sobel et al. | 206/380 |
| 5,052,551 | 10/1991 | Cerwin | 206/63.3 |
| 5,056,658 | 10/1991 | Sobel et al. | 206/63.3 |
| 5,131,533 | 7/1992 | Alpern | 206/63.3 |

Primary Examiner—Jimmy G. Foster
Attorney, Agent, or Firm—Robert L. Minier

[57] ABSTRACT

A suture package for a suture with attached needle The package allows for removal of the needle and attached suture from the package with a forceps without the user having to touch either the needle or the suture.

9 Claims, 3 Drawing Sheets

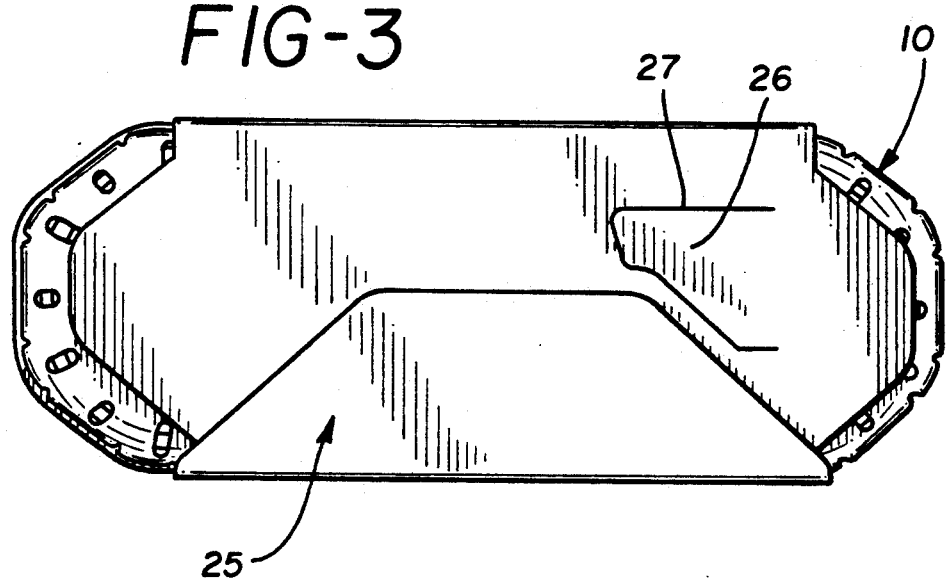
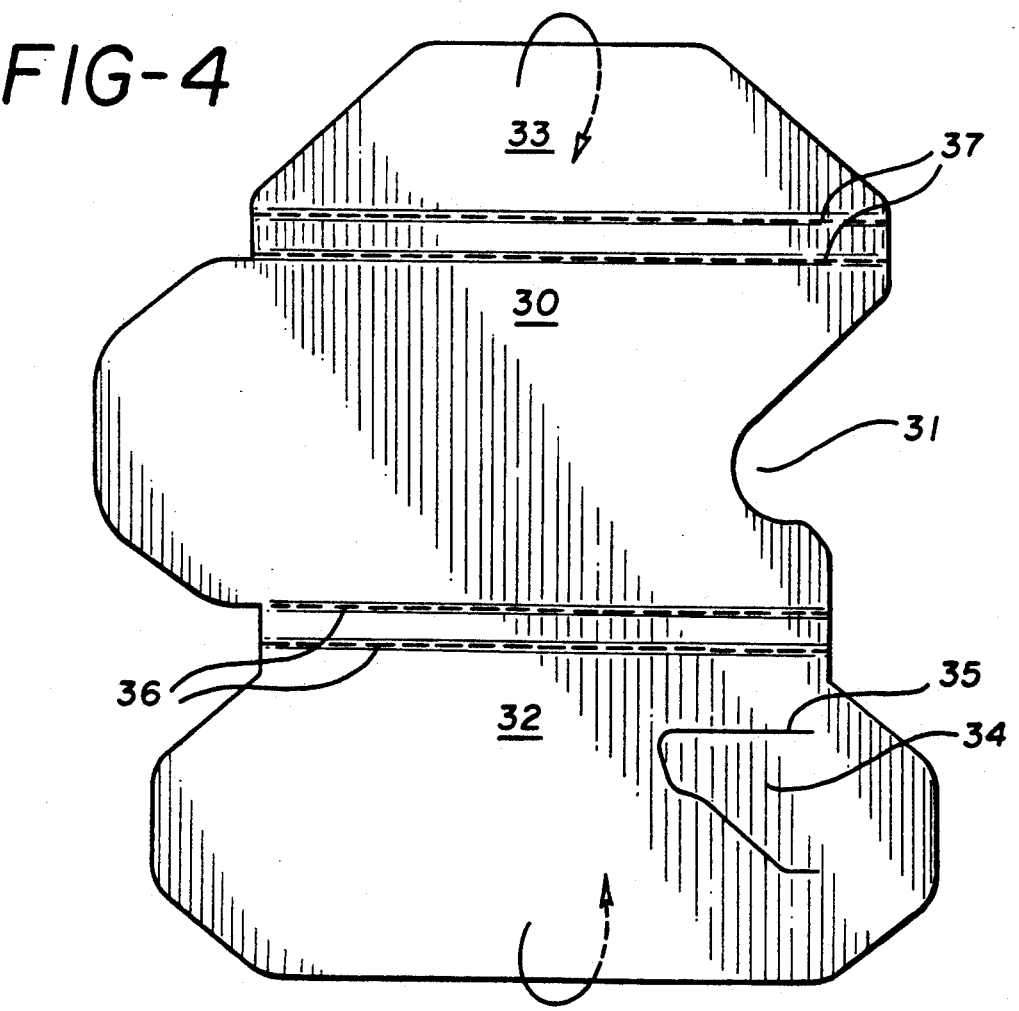

NO TOUCH SUTURE PACKAGE

FIELD OF THE INVENTION

A suture package for holding a sterile suture with an attached needle.

BACKGROUND OF THE PRESENT INVENTION

In the packaging of sutures with attached needles, it is important that the needle and its attached suture be easily removable from the package with a minimum of effort. Once the needle is grasped by a forceps and pulled, the needle should easily release from the package and allow the suture to be withdrawn. It, of course, is desirable to keep the requirement for touching the needle or adjusting the needle within the forceps or needle holder to a minimum. Also, it would be desirable to be able to grasp the needle in a manner, when removing it from the package, so that it would not have to be readjusted when the surgeon desires to use the needle to suture or join tissue.

Suture packages which allow for easy removal of the suture are well known. Such packages are described in U.S. Pat. Nos. 4,961,498; 4,967,902; 5,052,551; 5,056,658 and 5,099,994. All of these packages allow for ready removal of the suture once the needle has been grasped by a forceps or a needle holder. However, none of these prior art packages insure that the needle may be grasped one time and the suture removed from the package and the needle be in a position ready to be used for suturing. Generally, all of these packages require that the needle be touched or positioned in the forceps or needle holder to allow the suture to be removed from the package or the needle will have to be repositioned within the forceps before being used for suturing.

It is an object of the present invention to provide a suture package that allows the needle to be grasped and the suture removed without having to touch the needle. It is an object of the present invention to reduce the possibility that the user may be pricked by a needle. It is a further object of the present invention to reduce the possibility that a needle will have to be repositioned within the forceps before being used for suturing.

SUMMARY OF THE INVENTION

In accordance with the present invention, a suture package for holding a suture with an attached needle is provided. The package comprises a suture holder member. Preferably, the suture holding member has an oval shape. The member has a flat bottom section and means disposed on one side of said flat bottom section for holding the suture and displaying the needle on that side. In the preferred embodiment of the present invention, when the suture holder member is oval, the suture is held around the periphery of the oval member. A portion of the flat bottom of the suture holding member is deflectable out of the plane of the bottom. This deflectable portion underlies the needle. The suture holding member is encased in a protective sleeve. The sleeve comprises a top, a bottom, and two longitudinal sides. The longitudinal sides connect the top and bottom so that the suture holding member may be positioned within the sleeve. In a preferred embodiment of the sleeve, a portion of the top is cut away. The cut away portion overlies at least a portion of the needle so that the needle is exposed and will be readily grasped without having to tear or remove any of the protective sleeve The bottom of the protective sleeve also includes a deflectable portion. This deflectable portion in the sleeve underlies the deflectable portion in the suture holding member. In a preferred embodiment of the package, the deflectable portion in the sleeve is slightly larger than the deflectable portion in the suture holding member so that when the suture holding member is in the sleeve the bottom of the suture holder and the bottom of the sleeve will only deflect in one direction. Hence, in such a preferred embodiment when the needle is to be grasped by a forceps, the forceps can deflect both the bottom of the suture holding member and the sleeve and obtain a good "bite" or grasp on the needle. When the protective sleeve deflectable portion is slightly larger than the suture holding member deflectable portion, it insures that the holder of the package will not deflect or disrupt the positioning of the needle in the suture holder by inadvertently pressing the deflectable portion. In use, the user can take forceps and grasp the needle at any place along the length of the needle that is disposed in the cut out section. The user may grasp the needle to any desired depth within the jaws of the forceps so that an adequate "bite" and a correct positioning of the forceps is obtained. Once obtained, it is a simple matter to pull the suture from the package and have it already positioned in the forceps ready for suturing. This is accomplished without any touching of the needle by the user and requires no repositioning of the needle within the forceps prior to suturing.

BRIEF DESCRIPTION OF THE DRAWINGS

FIG. 3 is a bottom plan view of the suture holding member in the sleeve depicted in FIG. 2;

FIG. 4 is a plan view of the unfolded sleeve used with the suture holding member depicted in FIG. 1;

DETAILED DESCRIPTION OF THE DRAWINGS

Figure 1:
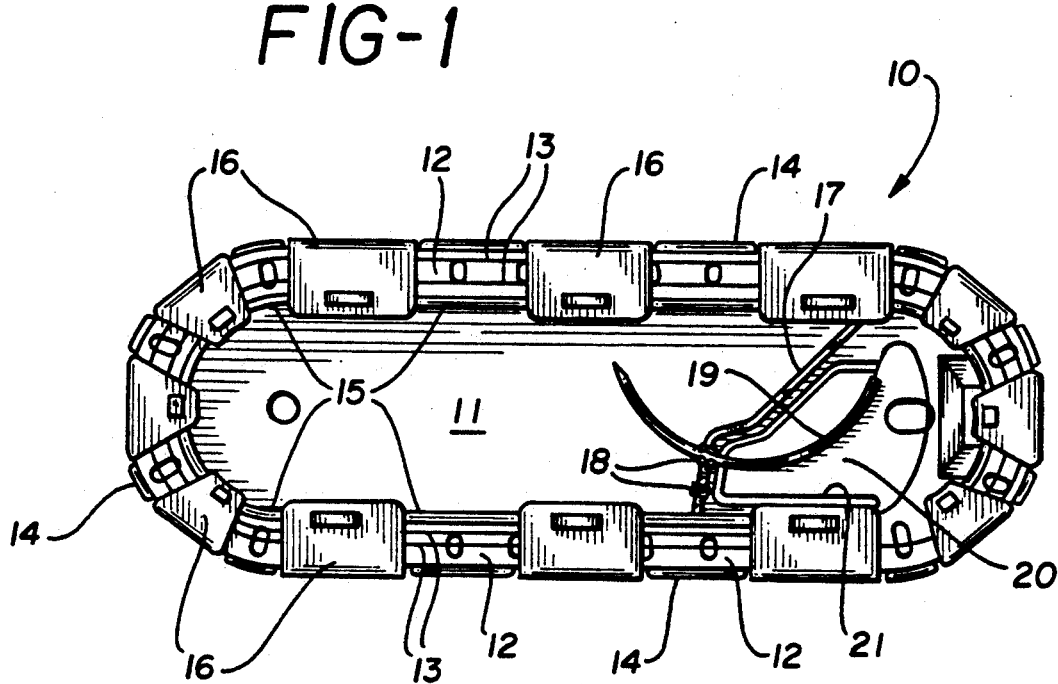
FIG. 1 is a plan view of a suture holding member according to the present invention.

Referring to FIG. 1, there is shown a suture holding member 10 in accordance with the present invention. The holding member is generally oval in shape though other shapes may be used. The member has a flat bottom section 11 with holding means 12 for one or more sutures 13 disposed around the periphery of the flat bottom section. The holding means comprises a first upwardly extending wall 14 disposed at the periphery of the flat bottom section and a second upwardly extending wall first disposed inwardly from the outer periphery of the holding member. Spaced around the periphery are a plurality of hinged door members 16. Once the suture is wound and placed in the channel formed by the outside of the flat bottom member, and the inwardly spaced well, the hinged doors may be folded over on top of the suture and locked in place. Also disposed at one end of the flat bottom section is a second upwardly extending wall 17 having a plurality of cut out areas 18 for a holding needle 19 as shown. In practice, the suture is wound about the outer periphery and in the channel as previously described and the needle then placed appropriately with a portion of it being held by one of the cut outs in the upwardly extending wall. Disposed beneath the needle is a deflectable portion 20. This deflectable portion is formed by the cut 21 so that the deflectable portion underlies the needle.

Figure 2:
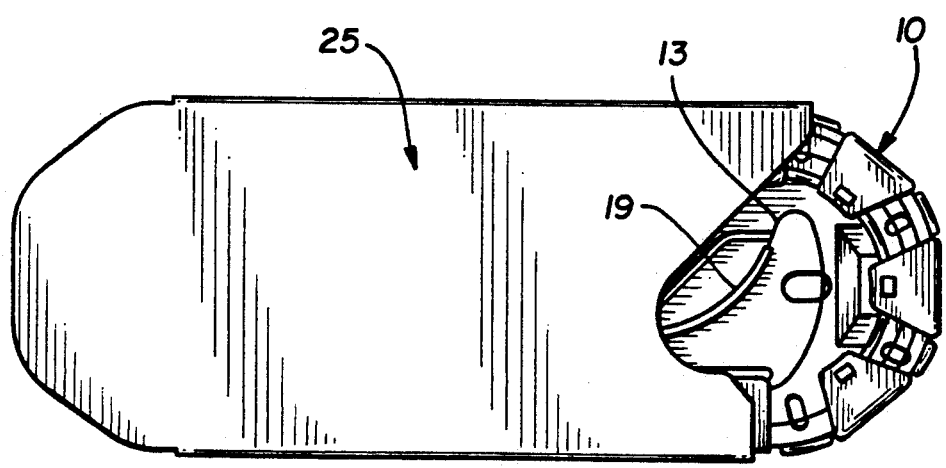
FIG. 2 is a top plan view of the suture holding member depicted in FIG. 1 in a sleeve in accordance with the present invention.

As shown in FIGS. 2 and 3, the suture holding member 10 depicted in FIG. 1 is encased or enclosed in a protective sleeve 25. The sleeve may be made from Kraft sulfite board or similar material. The sleeve overlies the top of the suture holding member but has a cutout at one end thereof to expose the needle 19. As seen in FIG. 3, the bottom of the sleeve includes a deflectable portion 26 formed by the cut 27. The deflectable portion of the sleeve underlies the deflectable portion in the suture holding member. The deflectable portion in the sleeve is slightly larger than the deflectable portion in the suture holding member. It is a simple matter when the user desires to extract the needle and suture from the package, to grasp the needle with forceps. Because the area underlying the needle is deflectable, the forceps can be placed as deep as desired on the needle so that the needle only needs to be grasped once by the forceps and the needle and suture removed from the package and the needle and suture ready for use. Because the deflectable portion of the sleeve is slightly larger, it will prevent inadvertent dislodgment of the needle should the user happen to place a finger on the deflectable portion on the sleeve, it will not deflect the deflectable portion of the suture holder. Hence, the deflectable portions of both the suture holder and the sleeve only deflect in one direction.

As seen in FIG. 4, the sleeve comprises a center panel 30 which has a cutout portion 31 that overlies one end of the top of the suture holding member. Two side panels 32 and 33 are attached to the center panel. One side panel 32 covers substantially the entire bottom of the cut 35 of the suture holding member and has a deflectable portion 34 formed by the cut 35. The other side panel 33 overlies the first side panel and may be glued or adhered thereto to form the sleeve. A pair of parallel fold lines 36 and 37 separate the side panels from the center panel to provide the desired depth to the sleeve.

Figure 5:
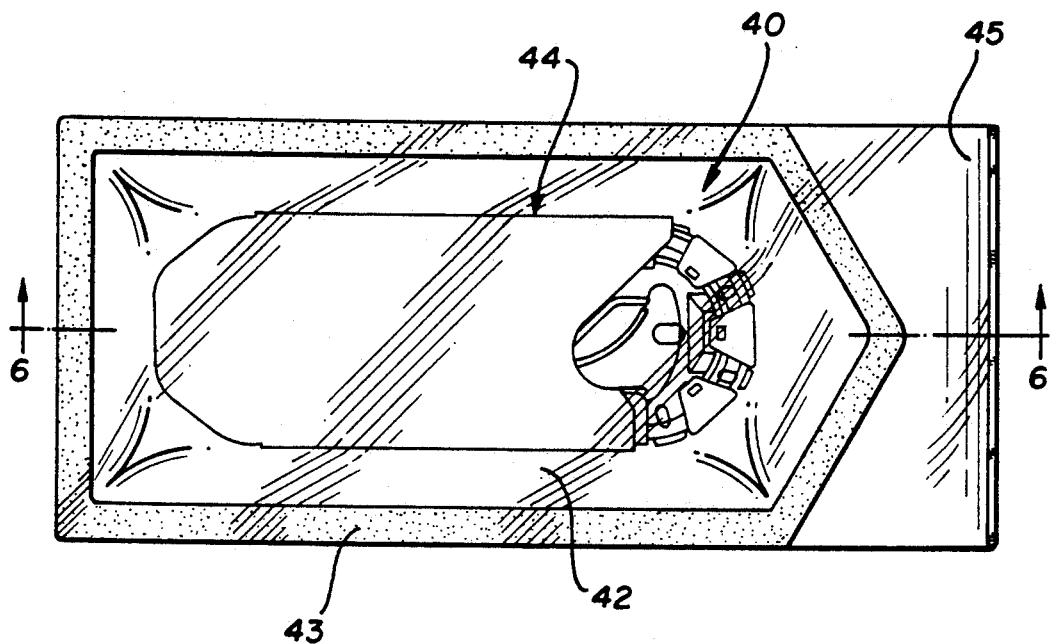
FIG. 5 is a plan view of the suture holding member of the sleeve of the present invention in a sterile package.
Figure 6:
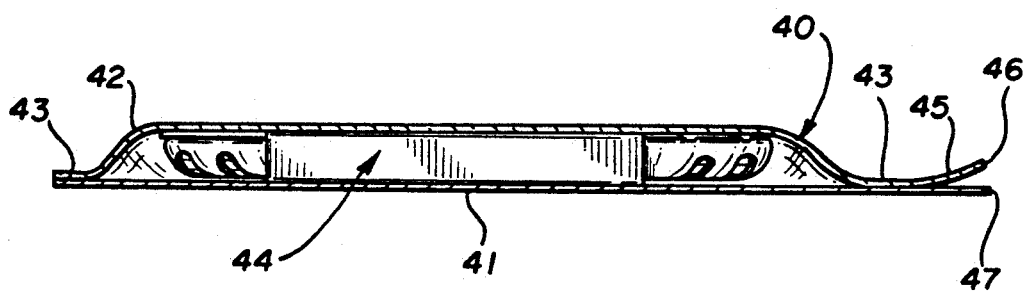
FIG. 6 is a cross-sectional view taken along lines 6—6 of FIG. 5.

The suture package described with respect to FIGS. 1 through 3 may be further packaged in a sterile package as is well known in the art. A suitable sterile package is depicted in FIGS. 5 and 6. The outer package 40 comprises a bottom paper or nonwoven fabric layer 41 and a top layer 42, preferably transparent film. The two layers are heat sealed 43 together about their periphery with the suture package 44 of the present invention disposed between the layers. At one side thereof, the heat sealed area is disposed inwardly from the edges of the top and bottom layers to provide a gripping area 45 and allow for easy opening of the package. A user may grasp the non heat-sealed ends 46 and 47 of the top and bottom layer respectively, peel the top layer off and place a sterile suture package of the present invention in a sterile field. It is then a simple matter for the nurse or other user who needs to remove the suture and needle from the package to grasp the needle at an appropriate position with a needle holder or pair of forceps and remove the needle and suture from the suture package and present it to the surgeon for suturing. In so doing, there has been no touching of the needle, either prior to or during the suturing operation.

While the outer package has been described with regard to a paper layer and a transparent film, other materials also could be used. For example, the two layers could be foil layers having their inside surfaces coated with appropriate heat sealable coatings. The bottom foil layer could be formed with a cavity for holding the suture package of the present invention. The upper film could then be heat sealed to the lower film around the periphery of the cavity to produce a sterile package. It is preferred, especially with heat sensitive sutures, that the heat sealing be spaced a distance away from the cavity. It is also desirable to keep the cavity as small as possible so that the suture package of the present invention fits snugly in the cavity. A snug fit allows greater control of the opening of the package and presentation of the suture and needle from the package.

The suture holder of the present invention may be made from any of the various plastic materials. A preferred plastic material is polypropylene because of its flexibility and moldability, ability to form a hinge, etc. The sleeve as previously mentioned is preferably made from Kraft sulfite board. The outer package may be made from any of the materials used in suture packaging as are well known in the art such as paper, nonwoven fabric, thermoplastic film, foils, and the like.

The invention described and the specific details and the manner in which it may be carried out having been exemplified it will be readily apparent to those skilled in the art that innumerable variations, modifications, and extensions of the basic principles involved may be made without departing from the spirit and scope of the present invention.

What is claimed is:

1. A suture package for a suture with an attached needle, said package comprising a suture holding member, said member having a flat bottom section and means disposed on one side of said bottom section for holding the suture and displaying said needle on said side, a portion of said flat bottom section underlying said needle being deflectable out of the plane of said flat bottom section and a protective sleeve member enclosing said suture holding member said sleeve having a top, bottom, and two longitudinal sides connecting said top and bottom, said bottom having a deflectable portion underlying the deflectable portion of said suture holding member.

2. A suture package according to claim 1 wherein the suture holding member has a substantially oval shape and the means for holding said suture are disposed around the periphery of said oval shaped suture holding member.

3. A suture package according to claim 1 wherein the protective sleeve member has a cut out portion on the top of said protective sleeve for exposing said needle on said suture holding member.

4. A suture package according to claim 1 wherein the deflectable portion on the protective sleeve member is larger than the deflectable portion on said suture holding member.

5. A suture package according to claim 1 wherein the suture holding member has an oval shape and the means disposed on one side of said flat bottom section are disposed around the periphery of the oval shape suture holding member, the protective sleeve member includes a cut out portion on the top of said protective sleeve member for exposing said needle and the deflectable portion of said protective sleeve is larger than the deflectable portion of the suture holding member.

6. A suture package comprising an outer package and a sterile inner package, said outer package comprising a bottom layer and a top layer, said layers being heat sealed together around the periphery of said layers, said inner package being sterile and being disposed between said top and bottom layers, said inner package comprising a suture holding member, said member having a flat bottom section and means disposed on one side of said flat bottom section for holding a suture and displaying said needle on said side, a portion of said flat bottom section underlying said needle being deflectable out of the plane of said flat bottom section and a protective sleeve member surrounding said suture holding member, said sleeve having a top, bottom, and two longitudinal sides connecting said top and bottom, said bottom having a deflectable portion underlying the deflectable portion of said suture holding member.

7. A suture package according to claim 6 wherein the top and bottom layers of said outer package are heat sealed together inwardly from one edge of said package to provide an unsealed area that may be grasped to peel the two layers apart.

8. A suture package according to claim 6 wherein the suture holding member has an oval shape and the means disposed on one side for holding said suture is disposed about the periphery of the oval shaped suture holding member, the protective sleeve includes a cut out portion on the top of said sleeve for exposing said needle and the deflectable portion of said protective sleeve is larger than the deflectable portion of said suture holding member.

9. A suture package according to claim 8 wherein the top and bottom layers of said outer package extend beyond the heat sealed portion at one side thereof to provide a grasping area to allow the top and bottom layers to be peeled apart.

* * * * *